(12) United States Patent
Lichten

(10) Patent No.: US 9,610,296 B2
(45) Date of Patent: Apr. 4, 2017

(54) INDUCING LACTATION IN NURSING FEMALES

(71) Applicant: Edward M. Lichten, Birmingham, MI (US)

(72) Inventor: Edward M. Lichten, Birmingham, MI (US)

( * ) Notice: Subject to any disclaimer, the term of this patent is extended or adjusted under 35 U.S.C. 154(b) by 0 days.

(21) Appl. No.: 14/613,741

(22) Filed: Feb. 4, 2015

(65) Prior Publication Data

US 2015/0216880 A1  Aug. 6, 2015

Related U.S. Application Data

(60) Provisional application No. 61/935,598, filed on Feb. 4, 2014.

(51) Int. Cl.
*A61K 31/58* (2006.01)
*A61K 9/00* (2006.01)
*A61K 9/06* (2006.01)

(52) U.S. Cl.
CPC ............ *A61K 31/58* (2013.01); *A61K 9/0014* (2013.01); *A61K 9/06* (2013.01)

(58) Field of Classification Search
CPC ......... A61K 31/58; A61K 9/06; A61K 9/0014
See application file for complete search history.

(56) References Cited

U.S. PATENT DOCUMENTS

| 2,589,898 | A | * | 3/1952 | Turner | .................. A23K 1/165 514/170 |
| 2007/0207197 | A1 | * | 9/2007 | Villarreal | ............. A61K 9/0014 424/450 |
| 2009/0202645 | A1 | * | 8/2009 | Predieri | ............... A61K 9/0019 424/489 |

FOREIGN PATENT DOCUMENTS

WO    WO 9808547 A1 *  3/1998 ............. A61K 31/58

OTHER PUBLICATIONS

Drugs and Breastfeeding, edited Sep. 2013.*
Lipoderm Ultra Review; published Nov. 13, 2016.*

\* cited by examiner

*Primary Examiner* — Sarah Pihonak
*Assistant Examiner* — Jason A Deck
(74) *Attorney, Agent, or Firm* — The Weintraub Group, P.L.C.

(57) ABSTRACT

A topical cream applied to a nipple of a lactating female induces lactation. The cream comprises a base cream having from about 0.5% to about 10%, by volume, of a steroid, based upon the total volume of the cream. The preferred steroid is stanozolol. Preferably, the cream comprises at least about 1% to about 10%, by volume, of stanozolol, based on the total volume of the cream.

5 Claims, No Drawings

INDUCING LACTATION IN NURSING FEMALES

CROSS REFERENCE TO RELATED APPLICATION

This application is a completion application and claims the benefit of U.S. Provisional Patent Application Ser. No. 61/935,598, filed Feb. 4, 2014 for "Induction of Lactation in Nursing Females" and is related to the subject matter of co-pending U.S. patent application Ser. No. 13/745,934, filed Jan. 21, 2013, the disclosures of both are hereby incorporated by reference in their entireties.

BACKGROUND OF THE INVENTION

In the above-referenced related application there is disclosed the use of a topical cream for the treatment of HSDD in women. As disclosed, the cream thereof is directed to causing a local physiological effect that stimulates the vagal nerves to mediate the neuropeptides that are linked to the brain for controlling oxytocin release.

It has now been found that the cream thereof generates an increase in the release of oxytocin in nursing females. The oxytocin release causes an induction of lactation.

SUMMARY OF THE INVENTION

In accordance herewith there is provided a topical cream, which when applied to the nipple(s) of a nursing female, induces increased lactation.

The cream, generally, comprises: (a) a base cream having from about 0.5% to about 10%, by volume, of a steroid, based upon the total volume of the cream; and (b) preferably, at least about 1% to about 10% by volume, of the steroid, based on the total volume of the cream.

The steroid used herein is preferably an androgen and, most preferably, stanozolol.

For a more complete understanding of the present invention, reference is made to the following detailed description and the accompanying example.

DESCRIPTION OF THE INVENTION

As noted above, the cream hereof, generally, comprises: (a) a base cream having from about 0.5% to about 10%, by volume, of a steroid, based upon the total volume of the cream; and (b) preferably, from at least about 1% to about 10% by volume, of a steroid, based on the total volume of the cream.

The steroid used herein is, preferably, an androgen and, is selected from the group consisting of, stanozolol, danazol and furazobol.

More particularly, in preparing the topical cream hereof, a commercially available base cream is used. Commercially available base creams, as is known to the skilled artisan, include emollients, water, alcohols, such as isopropyl alcohol and benzyl alcohol, glycerol, fragrances, moisturizers and the like as well as mixtures thereof.

A particularly preferred base cream is that sold under the mark Lipoderm. Lipoderm is reported as having two forms, Lipoderm Ultra and Lipoderm Y, each, comprising a proprietary blend of yohimbine HCl, caffeine, synephrine, acetyl L-carnitine, lecithin, sesamin, octopamine HCl and ascorbyl palmitate.

It should be noted that the base cream may be used alone or in admixture with other creams such as commercially available face creams, body moisturizing creams and the like, as well as mixtures thereof.

Where used the base cream and other additional cream may be used in any amount up to about a 50:50 volumetric mixture thereof of base cream to additional cream.

The androgen, which is, preferably, stanozolol, is present in an amount ranging from about 0.5% to about 10%, by volume, based on the total volume of the topical cream. It should be noted that other steroids, such as danazol, furazobol, and the like may be used in lieu of the stanozolol, while effective, they are to a lesser degree.

Preferrably, the stanozolol is used alone, although it may be used in conjunction with the danazol and/or the furazobol.

Also, as noted above, the danazol or furazobol may be substituted for the stanozolol in the same amounts as the stanozolol.

The stanozolol cream hereof is prepared by admixing, at room temperature, the base cream and the stanozolol. Any other ingredients or adjuvants, where used, are added thereto and stirred to form a homogenous composition.

It is hypothesized that there is a local physiological effect whereby stanozolol releases testosterone which triggers a spinothalmic tract which, in turn, activates oxytocin related axons from the brain and, thus, serves as a neuropeptide mediator. Concomitantly the stanozolol minimizes the effect of the sex hormone binding globulin in the cell wall. These effects induce lactation when the cream is applied to a women's nipple prior to nursing.

In use, the cream is applied to a nipple prior to breast feeding. Generally, the cream is left on the nipple for about five to about twenty minutes and, usually, for about five to about fifteen minutes.

It is then removed by washing. Then the mother is then ready to being nursing.

The utilization of the cream is continued, as needed, until adequate lactation is achieved.

For a more complete understanding of the present invention reference is made to the following illustrative Example. In the Example all parts are by volume, absent indications to the contrary.

EXAMPLE

A nursing mother having a six-month old child with the ability to achieve adequate lactation has applied a 2 ml quantity of a Lubriderm Ultra cream having two percent, by volume, stanozolol added thereto. The so-applied cream is left on for about two minutes. It is then washed off.

Thereafter, the mother reported an increase in milk production.

From the above, it is to be appreciated that there is described herein a topical cream which has a positive effect on women having a need to stimulate adequate lactation.

Having, thus, described the invention what is claimed is:
1. A method for inducing lactation in a nursing female, comprising:
    applying to at least one nipple an effective amount of an androgen consisting of a stanozolol-containing topical cream, the cream comprising a blend of yohimbine HCL, caffeine, synephrine, acetyl L-carnitine, lecithin, sesamin, octopamine HCL and ascorbyl palmitate.
2. The method of claim 1 wherein the stanozolol is present in an amount ranging from about 1% to about 10%, by volume, based on the total volume of the cream.

3. The method of claim 1 which further comprises an additional cream selected from the group consisting of face creams and body moisturizing creams.

4. The method of claim 3 wherein the base cream and additional cream are used in a volumetric ratio of base cream to additional cream up to about 50:50.

5. The method of claim 1 wherein the cream is applied for a period of about five minutes to about twenty minutes and is then removed prior to nursing.

* * * * *